(12) United States Patent  
Tanabe (10) Patent No.: US 9,149,656 B2  
(45) Date of Patent: Oct. 6, 2015

(54) REAL-TIME THREE-DIMENSIONAL RADIATION THERAPY APPARATUS AND METHOD

(71) Applicant: Eiji Tanabe, Kawasaki (JP)

(72) Inventor: Eiji Tanabe, Kawasaki (JP)

(73) Assignee: Accuthera Inc., Kawasaki (JP)

( * ) Notice: Subject to any disclaimer, the term of this patent is extended or adjusted under 35 U.S.C. 154(b) by 552 days.

(21) Appl. No.: 13/742,303

(22) Filed: Jan. 15, 2013

(65) Prior Publication Data

US 2013/0336449 A1 Dec. 19, 2013

(30) Foreign Application Priority Data

Jun. 15, 2012 (JP) ................................. 2012-135745

(51) Int. Cl.
*A61N 5/10* (2006.01)

(52) U.S. Cl.
CPC ............ *A61N 5/1067* (2013.01); *A61N 5/1045* (2013.01); *A61N 5/1083* (2013.01); *A61N 2005/1061* (2013.01)

(58) Field of Classification Search
CPC . A61N 5/1067; A61N 5/1083; A61N 5/1042; A61N 5/1045; A61N 5/1048; A61N 2005/1061
USPC .................... 378/65; 600/427, 429
See application file for complete search history.

(56) References Cited

U.S. PATENT DOCUMENTS

| 6,144,875 A * | 11/2000 | Schweikard et al. .......... 600/427 |
| 7,346,144 B2 * | 3/2008 | Hughes et al. .................. 378/65 |
| 8,358,737 B2 | 1/2013 | Tanabe |

FOREIGN PATENT DOCUMENTS

| JP | 3053389 B | 6/2000 |
| JP | 3881199 B | 2/2003 |
| JP | 3748531 B | 4/2003 |
| JP | 3790481 B | 8/2003 |
| WO | WO-2008/053026 A1 | 5/2008 |

* cited by examiner

*Primary Examiner* — Jack Berman
(74) *Attorney, Agent, or Firm* — Orion Consulting, Ltd.; Joseph P. Farrar, Esq.

(57) ABSTRACT

A radiation therapy apparatus including a robot supporting a robot head; a therapeutic radiation source attached to the robot head; a collimator for adjusting a radiation field shape of therapeutic radiation radiated from the therapeutic radiation source; a first therapeutic radiation detector attached to the robot head; a couch configured to support a patient lying supine thereon; a second therapeutic radiation detector for detecting the therapeutic radiation, disposed opposite the first therapeutic radiation detector with the couch disposed therebetween; at least two X-ray sources and detectors for position detection of a marker and/or a treatment target; an image processor for reconstructing an image of the treatment target; and a CPU that computes the intensity, irradiation direction, dose, and dose distribution of the therapeutic radiation, and dose absorbed by the treatment target, radiation field shape, and position of the treatment target in real time for feedback to a next irradiation.

11 Claims, 8 Drawing Sheets

REAL-TIME THREE-DIMENSIONAL RADIATION THERAPY APPARATUS AND METHOD

CROSS-REFERENCE TO RELATED APPLICATION

This patent application is based on and claims priority pursuant to 35 U.S.C. §119 to Japanese Patent Application No. 2012-135745, filed on Jun. 15, 2012, the entire disclosure of which is hereby incorporated by reference herein.

BACKGROUND

1. Field

Aspects of the example implementations relate to a real-time three-dimensional radiation therapy apparatus and method for Intensity Modulated Radiation Therapy (IMRT). More particularly, the example implementations relate to a real-time three-dimensional radiation therapy apparatus and method that detects beam data such as radiation field shape, irradiation direction, intensity, dose, dose distribution, and the position and shape of a treatment target for each delivery of therapeutic radiation, and feeds these results back to the next irradiation in real time.

2. Related Art

Figure 10:
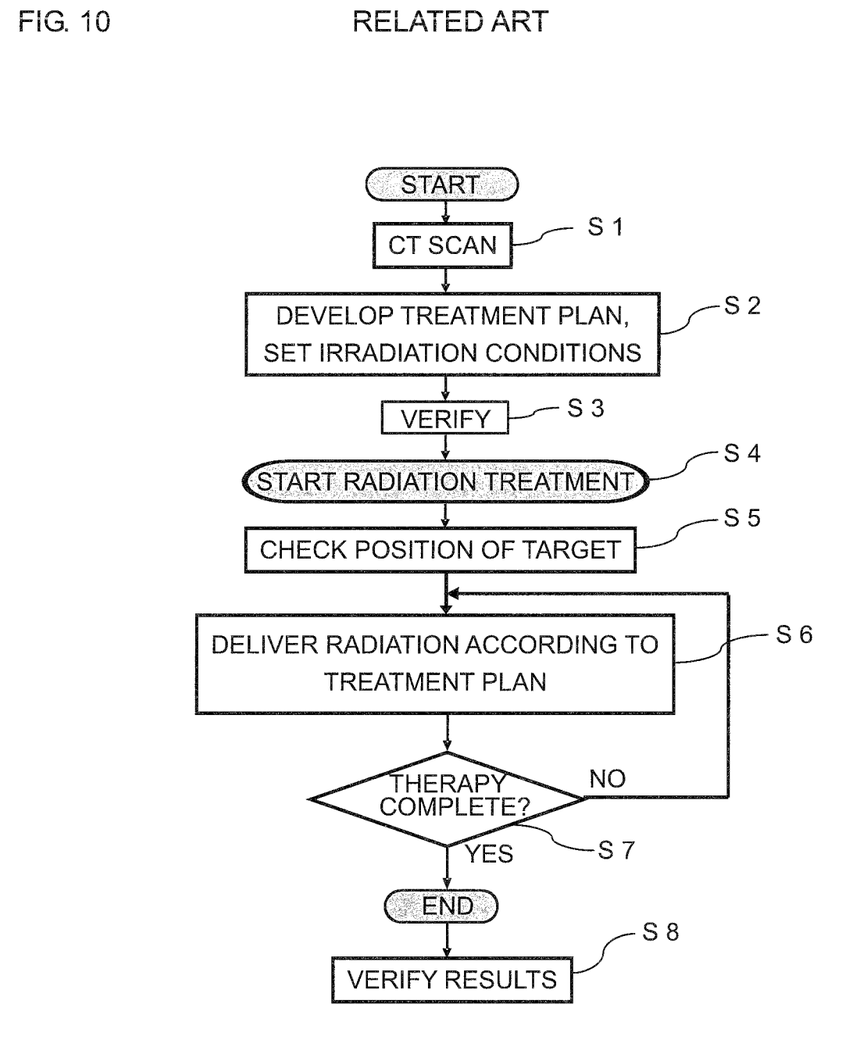
FIG. 10 is a flowchart showing steps in a related art radiation therapy method.

Radiation therapy is carried out, in general, in accordance with the flowchart shown in FIG. 10. Patients who undergo radiation therapy are subjected to detailed imaging of a treatment target using diagnostic imaging equipment including a CT scanner prior to the actual course of radiation treatment, in order to identify the treatment targets (step S1). The physician develops, on the basis of the image data obtained by the imaging, a treatment plan for determining a set of irradiation conditions such as the radiation field shape, irradiation direction, intensity, dose, and dose distribution of the radiation (step S2). Prior to carrying out the radiation therapy, the developed treatment plan is simulated using X-ray simulators, or measured and evaluated using a phantom, to verify the accuracy and validity of the treatment plan (step S3). In particular, in the case of IMRT, this pretreatment verification is important because of the complex combination of irradiation conditions. The related art preparation from imaging with a CT scanner through the completion of verification takes about one to two weeks. Next, the patient progresses to the step of radiation therapy (step S4). The patient is fixed in the same body position as the body position used in the development of the treatment plan and exposed to radiation (steps S5 and S6). The number of treatment sessions varies depending on the state of the disease. For example, in the case of prostate cancer, each individual treatment session lasts for approximately 20 minutes and is continued once a day for from 36 times to 39 times (steps S7 and S8). Therefore, a full course of therapy requires approximately seven to eight weeks.

The therapy requires such a long period of time because, with related art radiation therapy apparatuses, it is not possible to intensively irradiate only the tumorous tissue with a dose of radiation sufficiently high to kill only the tumorous tissue in a single exposure without also harming surrounding healthy tissue. Conventional radiation therapy apparatuses have radiation beam resolutions only on the order of 1 cm, and are thus unable to irradiate only tumorous tissue with a high degree of accuracy, not only in the case of tumorous tissue 1 cm or smaller in size but also at the boundaries between tumorous tissue and healthy tissue in the case of tumors larger than 1 cm. Thus, a dose of radiation that is low enough to not harm healthy tissue but which is still effective against tumorous tissue has to be delivered separately many times over multiple sessions. This divided irradiation thus kills the tumorous tissue by abnormal division, while the healthy tissue can recover even if it suffers some radiation damage.

Figure 8:
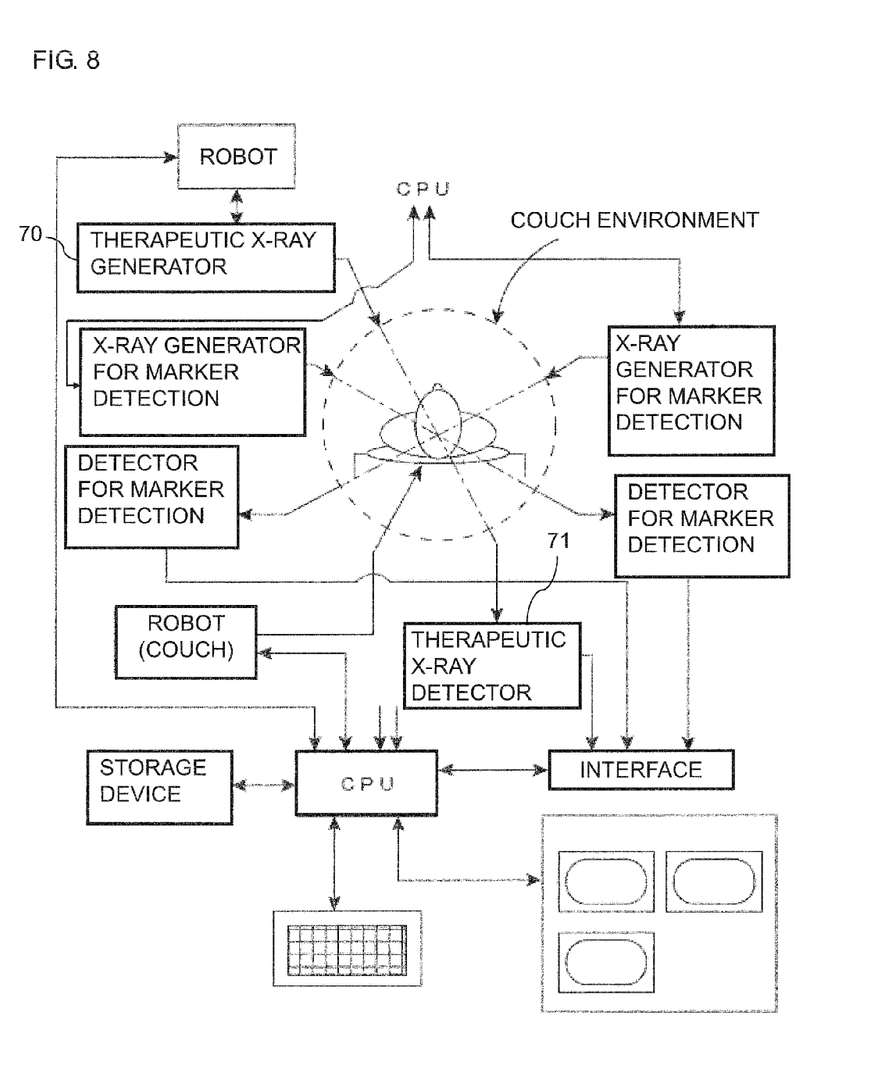
FIG. 8 is a diagram illustrating the configuration of a related art X-ray therapy apparatus.

The present applicant has previously filed an application for patent for an X-ray therapy apparatus which can track the movement of a treatment target of a patient in real time, and provide X-ray therapy at high speed with a high degree of accuracy from every direction to match the three-dimensional shape of the treatment target using high-power, small-diameter or small-breadth X-ray beams, titled "X-RAY THERAPY EQUIPMENT" (Japanese Patent Application No. 2009-75008), which was patented on Dec. 11, 2009 as Japanese Patent No. 4418888 (JP-4418888-B), and for which a corresponding U.S. patent issues on Jan. 22, 2013 as U.S. Pat. No. 8,358,737. The X-ray therapy apparatus described in JP-4418888-B includes an X-ray generation source for outputting high-energy X-rays of 1 MV or more, moreover while continuously varying the beam diameter or breadth of the X-rays in a range of from 1 mm to 10 mm. This X-ray generation source has made it possible to carry out X-ray irradiation with a high degree of accuracy to match the three-dimensional shape of the treatment target. The X-ray therapy apparatus described in JP-4418888-B includes, as shown in FIG. 8, a therapeutic X-ray sensor 71 for moving in conjunction with the movement of a therapeutic X-ray generator 70 while remaining opposite the therapeutic X-ray generator 70. This therapeutic X-ray sensor 71 is a sensor for detecting X-ray beam data such as the radiation field, intensity, direction, dose, and dose distribution of the therapeutic X-rays passing through the treatment target. The data acquired by this sensor is processed in real time and fed back to the next irradiation, thereby providing high-accuracy therapy.

However, the information on the therapeutic X-rays is only data on the therapeutic X-rays after the X-rays have passed through the treatment target; the actual dose absorbed by the treatment target has to be estimated from the treatment plan data. In addition, accuracy suffers because the irradiation direction of the therapeutic X-ray is detected in one plane only. Furthermore, in the X-ray therapy apparatus described in JP-4418888-B, the radiation field is formed by an X-ray tube array consisting of a bundle of X-ray tubes for outputting small-diameter or small-breadth X-ray beams, and thus, in the case of irradiating a large area, the procedure for forming the radiation field can be complicated.

As described above, the conventional radiation therapy requires a long period of time to completion. Therefore, in order to reduce the total therapy time, it has been proposed that the verification process prior to actual radiation treatment be shortened.

Thus, for example, the invention described in JP-2010-508106-A (national stage entry of PCT/EP2007/061787; published as WO/2008/053026) discloses a verification method that eliminates the need for the conventional measurement and evaluation using a phantom. The delivery of radiation is carried out toward a two-dimensional transmission detector, and on the basis of the detection results and data such as a beam model parameter, a beam model, and a mechanical parameter set, the fluence is calculated in accordance with a fluence calculation algorithm. Next, using the calculated fluence, three-dimensional image data including information on the shape and density of a treatment target, and a dose algorithm, the three-dimensional dose distribution is acquired with respect to the treatment target.

However, the three-dimensional dose distribution acquired in accordance with the dose algorithm is a calculated dose distribution, which is problematic in terms of accuracy because the actual dose may differ considerably from the calculated dose. Furthermore, the disclosure of JP-2010-508106-A fails to make any reference to post-treatment verification of results.

In short, the conventional art described above has several shortcomings. That is, conventional X-ray equipment suffers from inadequate detection accuracy of the therapeutic X-rays, that is, the X-rays used for treatment. More specifically, detection of radiated X-ray beam characteristics, such as radiation field shape, irradiation direction, intensity, dose, and dose distribution, as well as the dose absorbed by the treatment target, is inadequate because only the X-rays passing through the treatment target are detected. In addition, it is not possible to reduce the duration of a course of therapy without degrading the accuracy of the radiation treatment. Furthermore, the treatment plan and verification thereof, as well as verification of the therapeutic outcome after therapy, require substantial time and effort.

SUMMARY OF THE INVENTION

Accordingly, the present invention provides a radiation therapy apparatus optimized for IMRT that can track the movement of a treatment target in real time, and detect therapeutic radiation with a high degree of accuracy to feed the beam data back to the next set of irradiation conditions in real time, thereby providing radiation therapy at high speed with a high degree of accuracy.

Furthermore, the present invention also provides a radiation therapy apparatus and method that can substantially reduce the time and effort required to develop a treatment plan and carry out the data verification therefor, and the post-treatment verification of results.

More specifically, the present invention provides a radiation therapy apparatus having a first robot coupled to a robot head; a therapeutic radiation source; a collimator; a first therapeutic radiation detector; a second robot coupled to a support for a patient; a second therapeutic radiation detector; at least two X-ray sources for position detection; at least two X-ray detectors for position detection; an image processor; a central processing unit (CPU); and a control unit.

The therapeutic radiation source is attached to the robot head and radiates therapeutic radiation. The collimator adjusts a radiation field shape of therapeutic radiation radiated from the therapeutic radiation source and is attached to the robot head with the therapeutic radiation source disposed therebetween. The first therapeutic radiation detector is attached to the robot head, with the therapeutic radiation source and the collimator disposed therebetween. The second robot is coupled to the support for a patient, and configured to control the position and posture of the support. The second therapeutic radiation detector detects the therapeutic radiation and is disposed opposite the first therapeutic radiation detector, with the support disposed between the first and second therapeutic radiation detectors. The at least two X-ray sources emit low-energy X-rays for position detection toward either a marker embedded in the vicinity of the treatment target and/or the treatment target itself, disposed proximal to the patient on the support. The at least two X-ray detectors for position detection are attached proximal to the support and opposite the at least two X-ray sources for detecting the X-rays for position detection emitted by the X-ray sources for position detection, with each of the X-ray detectors disposed opposite a corresponding one of the X-ray sources with the support interposed therebetween. The image processor is configured to reconstruct an image of the treatment target and calculate position coordinates of the treatment target based on detection data from the at least two X-ray detectors. The CPU calculates beam intensity, irradiation direction, radiation field shape, dose, and dose distribution of the therapeutic radiation using detection data from the first and second therapeutic radiation detectors. The control unit controls the first robot, the second robot the first and second therapeutic radiation detectors, the X-ray sources for position detection, and the X-ray detectors for position detection.

The first therapeutic radiation detector detects therapeutic radiation delivered from the therapeutic radiation source immediately after the therapeutic radiation passes through the collimator. The second therapeutic radiation detector, which is proximal to the support with the patient lying thereon and opposite the first therapeutic radiation detector with the support interposed therebetween, tracks the movement of the therapeutic radiation source and detects the therapeutic radiation after the therapeutic radiation has passed through the treatment target. The CPU computes the intensity, irradiation direction, dose, and dose distribution of the therapeutic radiation, and dose absorbed by the treatment target, radiation field shape, and position of the treatment target in real time based on data output from the image processor and detection data from the first and second therapeutic radiation detectors, and feeds the calculation result back to a next irradiation of the therapeutic radiation in real time. The X-ray sources for position detection and the corresponding X-ray detectors for position detection are movable and controlled by the second robot so that irradiation directions and angles of the X-ray sources for position detection are symmetrically disposed on opposite sides of the treatment target of a patient on the support.

Additionally, the robot for therapeutic radiation source may be one of a multi-axis arm-shaped robot, a gantry-type robot, a C-arm robot, and a robot with a C-arm attached to an arm end of the multi-axis arm-shaped robot, to support the therapeutic radiation source, the collimator, and the first therapeutic radiation detector.

Additionally, the second therapeutic radiation detector may be supported by one of the gantry-type robot, the C-arm robot, and the robot with the C-arm attached to the arm end of the multi-axis arm-shaped robot.

Additionally, the collimator may be an iris collimator or a multileaf collimator made of a heavy metal, and continuously varies the shape of the beam emitted from the therapeutic radiation source.

Additionally, the collimator adjusts the diameter or breadth of the beams emitted from the therapeutic radiation source to provide a radiation field of from 1 mm to 50 mm in diameter or breadth on the treatment target.

Additionally, the collimator adjusts the diameter or breadth of the beams emitted from the therapeutic radiation source to provide a radiation field of from 1 mm to 10 mm in diameter or breadth on the treatment target.

Additionally, therapeutic radiation delivery is repeated about 250 times/second.

In addition, the present invention provides a radiation therapy method for the radiation therapy apparatus described above, comprising the steps of executing, in real time, a step of identifying a position and a shape of the marker and/or the treatment target using the X-ray sources for position detection and the X-ray detectors for position detection; setting a set of irradiation conditions for the therapeutic radiation; delivering the therapeutic radiation toward the treatment target from the therapeutic radiation source; acquiring beam data on the therapeutic radiation by the first and second therapeutic radiation detectors; updating a next set of irradiation conditions in real time on the basis of the beam data on the therapeutic radiation acquired in the acquiring step; and storing, in a storage device, data output from the X-ray detectors for position detection and the first and second therapeutic radiation detectors.

Additionally, the set of irradiation conditions may be updated on the basis of detection data from the X-ray detectors for position detection and detection data from the first and second therapeutic radiation detectors, with the radiation therapy method further comprising the step of stopping the delivery of therapeutic radiation from the therapeutic radiation source if the next irradiation area falls outside the treatment target.

Additionally, the method further comprises the step of using the detection data from the X-ray detectors for position detection and the first and second therapeutic radiation detectors stored in the storage device to verify the results of radiation therapy.

Additionally, the step of delivering the therapeutic radiation is repeated about 250 times/second.

According to the aspects described above, a radiation therapy apparatus and method optimized for IMRT can be provided that can track the movement of a treatment target of a patient in real time, and detect the beam data on therapeutic radiation and the position and shape of the treatment target to feed the data back to the next set of irradiation conditions in real time, thereby providing radiation therapy at high speed with a high degree of accuracy. The use of the radiation therapy apparatus makes it possible to deliver a high dose of radiation to the treatment target intensively with a high degree of accuracy, thereby succeeding in significantly reducing the number of radiation treatment sessions.

Furthermore, according to the aspects described above, the beam data on therapeutic radiation and the position and shape of the treatment target are detected in real time, and the result is fed back to the next set of irradiation conditions to achieve a high-accuracy radiation therapy, thereby succeeding in reducing the time and effort required to develop and verify the treatment plan as well as the post-treatment verification, and thus dramatically reducing the duration of therapy and consequently the burden on both the patient and the physician.

BRIEF DESCRIPTION OF THE DRAWINGS

A more complete appreciation of the invention and many of the advantages thereof are obtained as the same becomes better understood by reference to the following detailed description when considered in connection with the accompanying drawings, wherein.

DETAILED DESCRIPTION

Embodiments will now be described below in detail with reference to the drawings, in which the same components and functions are denoted by the same reference numerals.

In describing embodiments illustrated in the drawings, specific terminology is employed for the sake of clarity. However, the disclosure of this patent specification is not intended to be limited to the specific terminology so selected, and it is to be understood that each specific element includes all technical equivalents that have a similar function, operate in a similar manner, and achieve a similar result.

Figure 1:
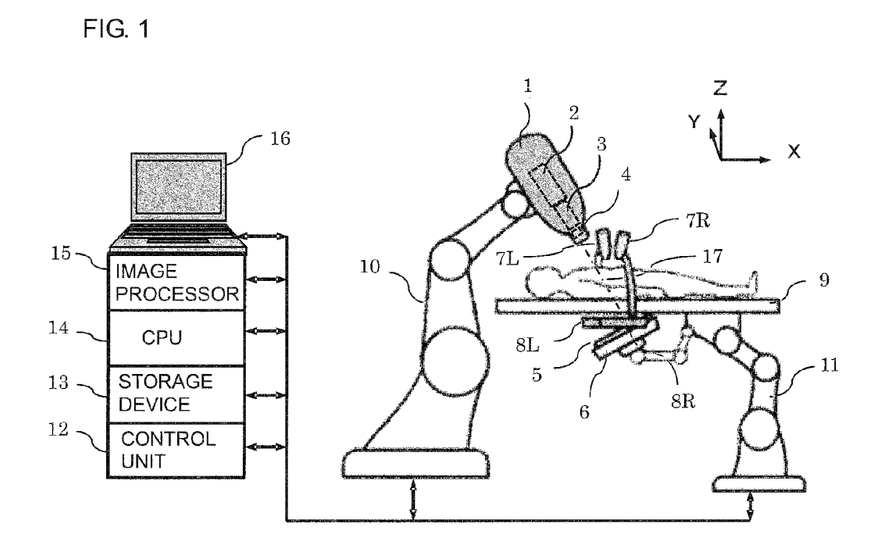
FIG. 1 is a diagram illustrating a radiation therapy apparatus according to embodiments.

FIG. 1 is a diagram illustrating a radiation therapy apparatus according to example embodiments. A robot head 1 is supported by an arm-shaped robot 10 of multiple axes (i.e., six or seven axes). The robot head 1 has a therapeutic radiation source 2 that generates therapeutic radiation, a collimator 3 for adjusting the radiation field exposed to radiation, and a first therapeutic radiation detector 4 for detecting the radiation passing through the collimator 3, which are each built into the robot head 1. The energy of the radiation radiated from the therapeutic radiation source 2 is on the order of 6 MV in the case of X-rays. The collimator 3 and the first therapeutic radiation detector 4 are placed in proximity to the therapeutic radiation source 2 as shown in FIG. 1, and have effective surfaces fixed at an angle perpendicular to a central axis 17 of the radiation radiated from the therapeutic radiation source 2.

A couch robot 11 supports a couch 9, moves the couch 9 in the X, Y, and Z axis directions, rotates about the Z axis, and controls the tilt with respect to the X axis and the Y axis. X-ray sources 7L, 7R for position detection may be installed on the sides of the couch, or near the couch 9 in a manner that can be controlled by the couch robot 11. In the configuration shown in FIG. 1, the X-ray sources 7L, 7R for position detection are fitted to both sides of the couch 9. The X-rays radiated from the X-ray sources 7L, 7R for position detection are low-energy X-rays, on the order of 100 kV.

X-ray detectors 8L, 8R for position detection may be installed on the bottom surface of the couch 9, or near the couch in a manner that can be controlled by the couch robot 11. In the configuration shown in FIG. 1, X-ray detectors 8R and 8L for position detection are fitted to the bottom of the couch, disposed opposite the X-ray source 7L for position detection and the X-ray source 7R for position detection, respectively. The X-ray sources 7L, 7R for position detection are angled so that radiated X-rays intersect at the treatment target. This intersection is coordinated by the couch robot 11, depending on the condition of the treatment target. The control of movements such as positions and orientations of the X-ray sources 7L, 7R for position detection and the X-ray detectors 8L, 8R for position detection is exercised by the couch robot 11 in accordance with signals from a control unit 12. The moving of the radiation fields of the X-ray sources 7L, 7R for position detection in response to the position of the treatment target can be implemented by a configuration for moving only the couch 9 with a patient lying supine thereon. Alternatively, the X-ray sources 7L, 7R for position detection and the X-ray detectors 8L, 8R for position detection may be movable and directed to the treatment target while the couch 9 is stationary. Yet alternatively, both the couch 9, on the one hand, and the X-ray sources 7L, 7R for position detection and the X-ray detectors 8L, 8R for position detection and the other may be movable.

Below the couch 9 a second therapeutic radiation detector 5 supported by the couch robot 11 is placed opposite the first therapeutic radiation detector 4, with the couch 9 interposed therebetween. A beam stopper 6 made of tungsten for absorbing therapeutic radiation is placed on the rear surface of the therapeutic radiation detector 5. The beam stopper 6 is placed so as to move with the therapeutic radiation detector 5. Although the robot head 1 moves and with it the radiation source 2 for generating therapeutic radiation, the collimator 3, and the first therapeutic radiation detector 4, nevertheless the opposed relationship between the first and second therapeutic radiation detectors 4 and 5 is maintained by the arm-shaped robot 10 and the couch robot 11 in accordance with signals from the control unit 12.

Figure 4:
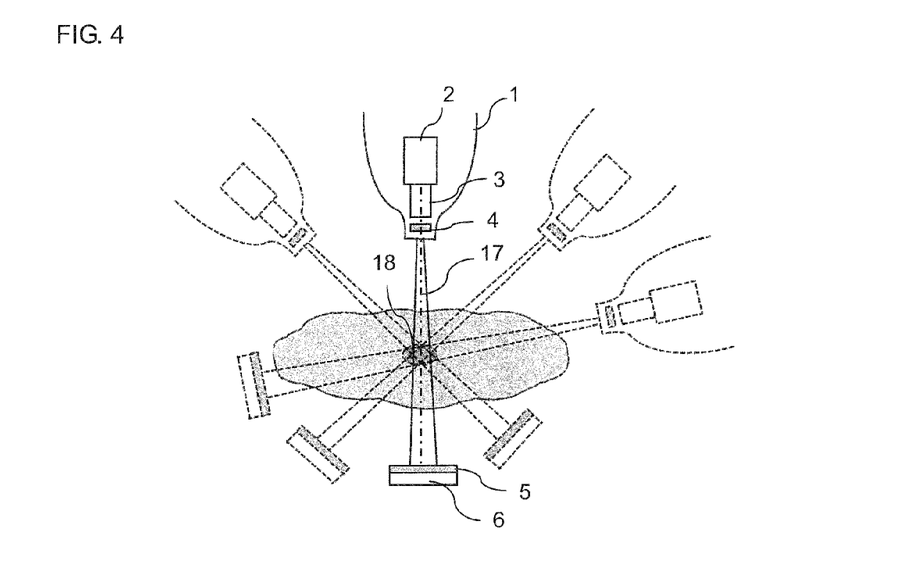
FIG. 4 is a diagram for explaining the detection of radiation in a radiation therapy apparatus according to the embodiments.

FIG. 4 shows a positional relationship among the therapeutic radiation source 2, the collimator 3, the first therapeutic radiation detector 4, the second therapeutic radiation detector 5, and the beam stopper 6. The collimator 3, the first therapeutic radiation detector 4, the second therapeutic radiation detector 5, and the beam stopper 6 are controlled by signals from the control unit 12 so that the respective effective surfaces remain perpendicular to the central axis 17 of the radiation radiated from the therapeutic radiation source 2.

In IMRT, the radiation is delivered toward a treatment target 18 from every direction in three dimensions. The first therapeutic radiation detector 4 and the second therapeutic radiation detector 5 are controlled so as to always remain opposite each other with the treatment target 18 interposed therebetween. Therefore, when the radiation is delivered from the back of a patient, that is, from below the couch 9, the second therapeutic radiation detector 5 and the beam stopper 6 are moved above the patient.

The first therapeutic radiation detector 4 can be implemented through the use of common optical fibers or scintillation fibers which transmit radiation. When light emitted in the case of radiation incidence onto the fibers is detected by a photo diode or a photomultiplier, the identification of the position of incidence of the radiation and the radiation intensity, the dose, and the dose distribution can be determined in real time. Alternatively, transmission ionization chambers and semiconductor detectors can be also employed as the first therapeutic radiation detector 4.

For the second therapeutic radiation detector 5, flat panel sensors may be employed. High-resolution flat panel sensors which operate at high speed are commercially available and have become widespread. In addition, the use of a photon detector as the second therapeutic radiation detector 5 can achieve even higher speed and an even higher degree of accuracy. Flat panel sensors are also usable for the X-ray detectors 8L, 8R for position detection. The X-ray detectors 8L, 8R for position detection are configured to identify the position and shape of a target or of a marker embedded in the vicinity of the treatment target, and therefore it is not always necessary to scan all of the pixels in the flat panel sensors. As a result, higher-speed operation can be implemented by appropriately selecting the pixels to be scanned.

The collimator 3 adjusts the beam diameter or breadth of the radiation delivered from the therapeutic radiation source 2. With the progress of medical technology in recent years, it is now possible to detect small tumors of 1 cm or less in diameter or breadth. In order to treat this small tumor, there is a need to make the beam diameter or breadth of the radiation considerably smaller than the size of the tumor that is the treatment target in order to eliminate the penumbra effect that is produced by high-energy X-rays scattering at the inner wall of the collimator 3 and penetrating the edge of the collimator 3. For example, for a tumor of 1 cm in diameter or breadth, the beam diameter or breadth of the radiation is desirably at least on the order of 1 mm in diameter or breadth. However, conventional multileaf collimators have a limitation on the order of 8 mm for the minimum beam diameter or breadth due to limitations on the thickness of the leaves. Moreover, the beam produced by such collimators has an angular shape. For this reason, it has not been possible to treat a curved tumor which has a size on the order of 1 cm.

Figure 5A:
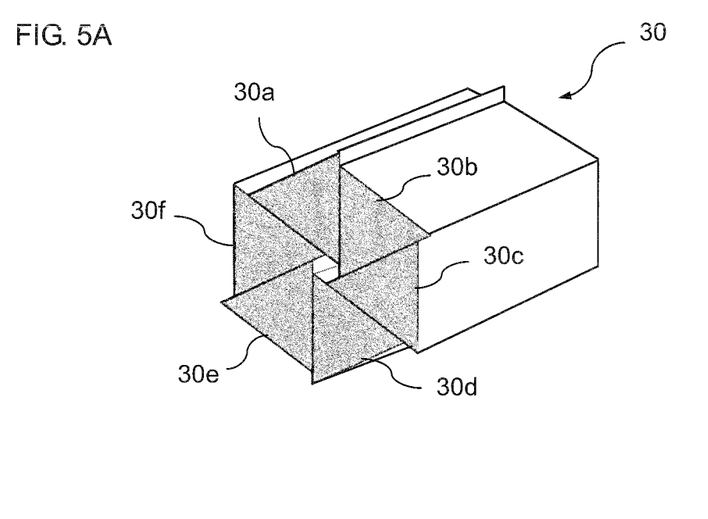
FIGS. 5A and 5B show a schematic perspective view of an iris collimator 30 preferred for the radiation therapy apparatus according to the example embodiment and an aperture area thereof, respectively.
Figure 5B:
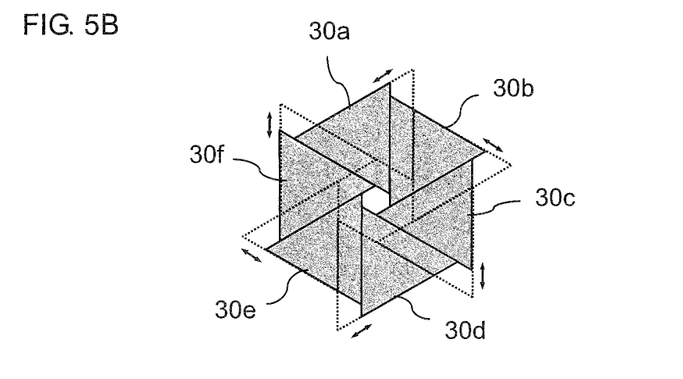

FIG. 5A shows a schematic perspective view of an iris collimator 30 used for the radiation therapy apparatus according to the present invention. FIG. 5B shows an aperture area thereof. It is to be noted that although FIGS. 5A and 5B show a case of six aperture leaves 30a, 30b, . . . , and 30f, the number of leaves may be changed appropriately. The size of the aperture of the iris collimator can be adjusted by sliding, in the directions of the arrows, linear slides (not shown) attached to the non-adjacent side surfaces on the outer perimeter of the respective leaves indicated by reference numerals 30a, 30b, . . . , and 30f in FIG. 5B. When the radiation is incident on the aperture area of the iris collimator, collimated radiation is emitted from the other aperture side. During radiation therapy, the radiation can be delivered accurately to match the shape of the treatment target by adjusting the aperture of the iris collimator 30 in accordance with the shape of the treatment target. The use of the iris collimator 30 can adjust the radiation field of the therapeutic radiation from 1 mm to 50 mm in diameter or breadth on the treatment target. For the material of the iris collimator, a heavy metal such as tungsten which absorbs radiation may be used. It is to be noted that although an iris collimator is used for the present embodiment, alternatively a multileaf collimator may be used instead provided that it is able to achieve a beam diameter or breadth of about 1 mm.

A central processing unit (CPU) 14 and an image processor 15 calculate the three-dimensional coordinates from the two-dimensional coordinates of the treatment target or maker using an algorithm such as Direct Linear Transformation (DLT) or the like from the output data from the X-ray detectors 8L, 8R for position detection. Furthermore, the units reconstruct projection data, and then convert the data into a three-dimensional image. A three-dimensional image of the marker or treatment target may be displayed on a monitor 16 (e.g., by a user) to confirm the position and shape of the image. In addition, the CPU 14 and the image processor 15 process detection data from the first and second therapeutic radiation detectors 4, 5 as input data, and output therapeutic radiation beam data such as the intensity, irradiation direction, radiation field shape, dose, and dose distribution of therapeutic radiation, and data on the position and shape of the treatment target.

In the radiation therapy apparatus according to the present invention, the first therapeutic radiation detector 4 acquires beam data on radiation immediately after being radiated from the collimator 3, whereas the second therapeutic radiation detector 5 acquires beam data on radiation after passing through the treatment target. As a result, dose absorbed by the treatment target can be thus known with good precision, as compared to a conventional radiation therapy apparatus. Furthermore, on the basis of the beam detection data from the first and second therapeutic radiation detectors 4, 5, the next irradiation can be corrected and updated for each delivery of therapeutic radiation, and it is thus possible to irradiate the treatment target accurately.

As described above, the radiation therapy apparatus according to the present invention is capable of accurate irradiation with small-diameter or small-breadth radiation beams, and can thus substantially reduce the damage to healthy tissue compared to a conventional radiation therapy apparatus. Therefore, the treatment target can be exposed to a high dose of radiation, and it is thus possible to complete the treatment with just a single dose of irradiation, as compared with a treatment program that divides the irradiation into 30 or more separate dosages as occurs in treatment with a conventional radiation therapy apparatus. In addition, as described above the radiation therapy apparatus according to the present invention can substantially reduce the duration of the radiation therapy compared to a conventional radiation therapy apparatus, and substantially reduce the burden on both patients and physicians. Furthermore, the cost of the therapy can be also reduced.

Figure 2:
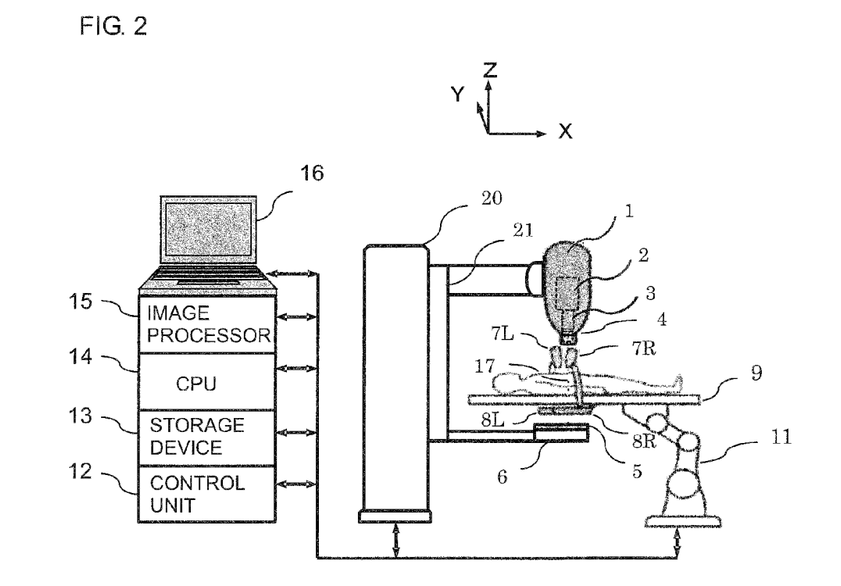
FIG. 2 is a diagram illustrating an embodiment as a gantry-type robot.

FIG. 2 shows an embodiment of the present invention as a gantry-type robot equipped with the therapeutic radiation source 2, collimator 3, first therapeutic radiation detector 4, and second therapeutic radiation detector 5 of the radiation therapy apparatus according to the present invention. In FIG. 2, a robot head 1 with the therapeutic radiation source 2, collimator 3, and first therapeutic radiation detector 4 built therein is attached to a rotating unit 21 of the gantry-shaped robot 20. The second therapeutic radiation detector 5 and a beam stopper 6 are also placed on the rotating unit 21 opposite the robot head 1. The rotating unit 21 rotates about a treatment target with the X axis as a central axis while maintaining the opposed relationship between the robot head 1 and the second therapeutic radiation detector 5. According to the present embodiment, the rotation of the rotating unit 21 and the oscillation of the robot head 1 exposes the treatment target to radiation from all angles.

Figure 3:
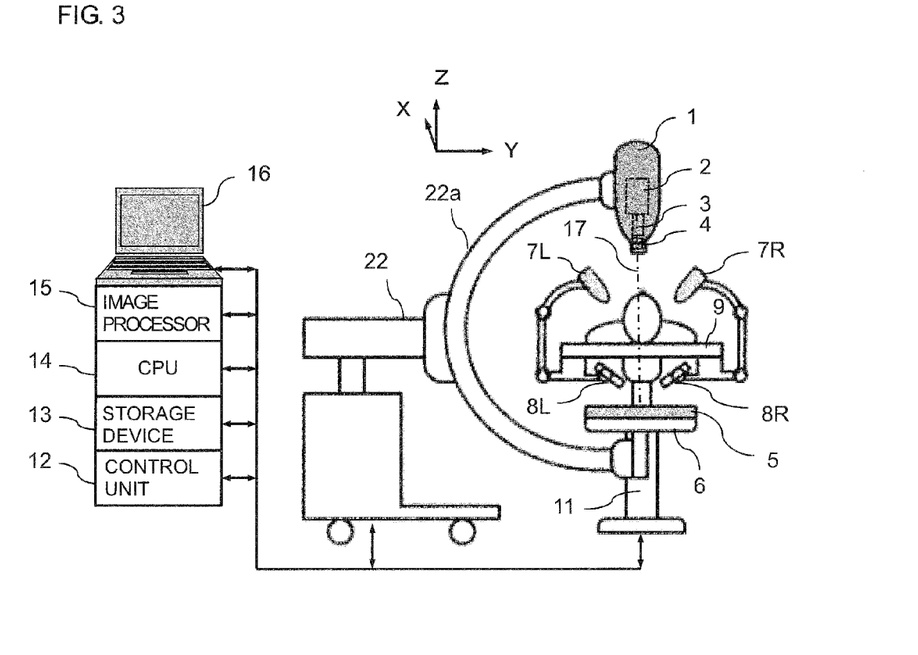
FIG. 3 is a diagram illustrating an embodiment as a C-arm robot.

FIG. 3 shows an embodiment of the present invention as a C-arm robot equipped with the therapeutic radiation source 2, collimator 3, first therapeutic radiation detector 4, and second therapeutic radiation detector 5 of the radiation therapy apparatus according to the present invention. In FIG. 3, a robot head 1 with the therapeutic radiation source 2, collimator 3, and first therapeutic radiation detector 4 built therein, and the second therapeutic radiation detector 5 and a beam stopper 6 are placed at opposite ends of a C-arm 22a while maintaining the opposed relationship therebetween. Therefore, the first and second therapeutic radiation detectors 4, 5 can always remain opposite each other, even when the C-arm 22a moves while rotating around a patient.

Moreover, as yet another embodiment, even when the robot equipped with a C-arm section as shown in FIG. 3 is applied to the ends of the arm-shaped robot 10 and couch robot 11 as shown in FIG. 1, the effect is the same as in the case of the embodiment illustrated in FIG. 1 and the embodiment illustrated in FIG. 3.

Figure 9:
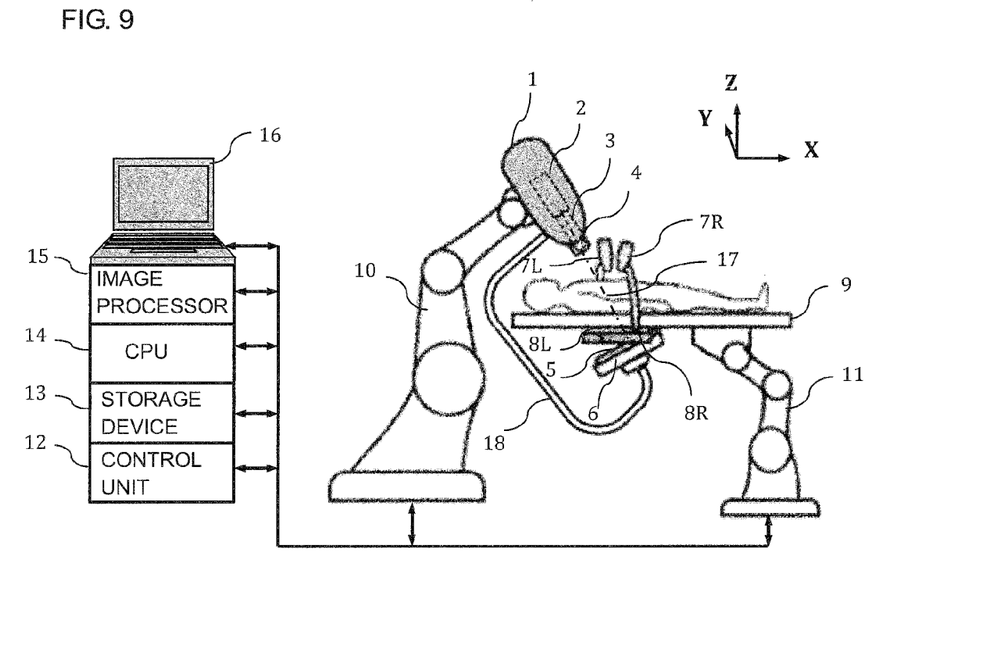
FIG. 9 is a diagram illustrating an embodiment of the radiation therapy apparatus configured with a second therapeutic radiation detector and a beam stopper 6 placed together at the opposite end of a C-arm attached to a robot head.

FIG. 9 shows yet another and further embodiment, with the second therapeutic radiation detector 5 and the beam stopper 6 placed together at the opposite end of a C-arm 18 attached to the robot head 1. In this configuration as well, the first and second therapeutic radiation detectors 4, 5 can always remain opposite each other.

Figure 6:
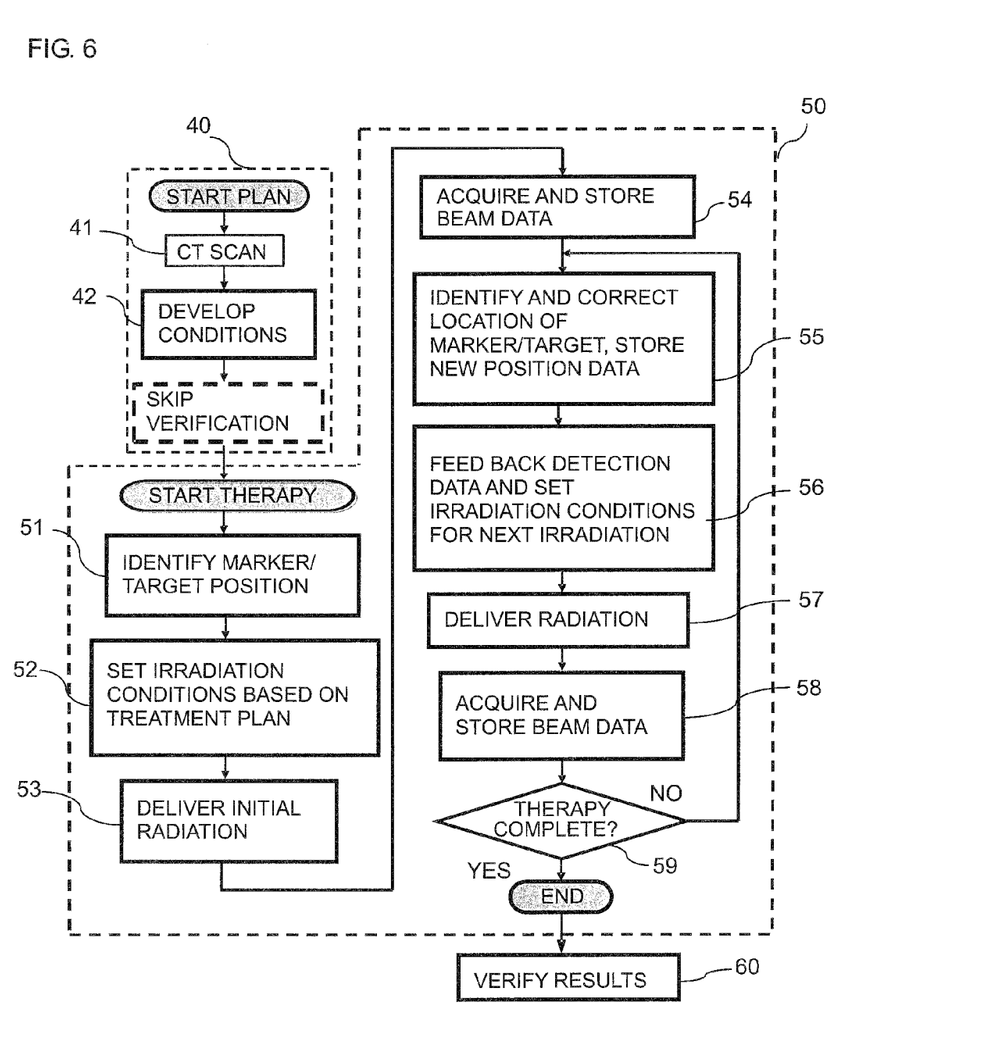
FIG. 6 is a flowchart showing steps in a radiation therapy method according to the example embodiment.

FIG. 6 shows steps in a process of providing radiation therapy using the radiation therapy apparatus according to the present invention. First, a physician develops a radiation treatment plan (operation group 40). In the development of a conventional treatment plan, a treatment target is subjected to imaging in detail using diagnostic imaging equipment including a CT scanner. Then, a determination is made, for example, by a physician, on the basis of the image, of a detailed method of treatment and the conditions thereof, such as the setting of the treatment target, the irradiation direction, intensity, radiation field shape, dose, and dose distribution of therapeutic radiation. At that time, movement of the treatment target due to breathing, etc., also have to be taken into consideration. In contrast, with the radiation therapy apparatus according to the present invention, the physician carries out imaging with a CT scanner (step 41) in order to set the treatment target, and then basically only has to determine the setting of the treatment target, and the irradiated point, irradiation direction, intensity, dose, and dose distribution of initial irradiation (step 42).

The treatment plan can be simplified in this way because, as illustrated in the radiation therapy step (step group 50), the CPU 14 detects and analyzes beam data on delivered therapeutic radiation and the position and shape of the treatment target for each delivery of therapeutic radiation in real time to determine the validity of the irradiation result, and feeds the results of that detection and analysis back to the next irradiation.

In the development of a treatment plan for conventional IMRT, there is a need to verify the validity of the treatment plan by simulating the validity of the absorbed dose in the treatment target using a simulator or by actually measuring the irradiation dose using a phantom, prior to implementing the developed treatment plan. In contrast, with the radiation therapy apparatus according to the present invention, basically, the prior verification step is not required because, as described above, while repeating the irradiation with X-ray for position detection and therapeutic radiation, data on the position and shape of the target and the beam data on the therapeutic radiation are analyzed by the CPU 14 for each irradiation in real time, and appropriately fed back to the next irradiation. Therefore, each delivery of therapeutic radiation is always carried out accurately, under optimum set of irradiation conditions. As described above, with the radiation therapy apparatus according to the present invention, the development of a treatment plan and the duration of the subsequent verification can be reduced substantially. Thus, the burden on the physician can be reduced substantially.

Next, actual radiation treatment is conducted (step group 50). The step group 50 will be described with reference to FIG. 6 and also FIG. 7, which shows a timing chart of the main steps in a program of radiation therapy. In conventional IMRT, there is a need to align the position of a treatment target of a patient lying supine on the couch with the position used in the development of a treatment plan prior to conducting actual radiation treatment. In contrast, with the radiation therapy apparatus according to the present invention, there is no need for such alignment of the treatment target with the position used in developing the treatment plan. With the radiation therapy apparatus according to the present invention, immediately prior to the delivery of therapeutic radiation, the treatment target is irradiated with low-energy X ray radiation from the X-ray sources 7L, 7R for position detection to image markers embedded in the vicinity of the treatment target, the treatment target itself, or both the markers and the treatment target. The X-ray sources 7L, 7R for position detection and the X-ray detectors 8L, 8R for position detection are controlled by the couch robot 11 and identify the position coordinates and the shape of the treatment target in real time in an independent three-dimensional coordinate system on the couch. The image data and position data on the treatment target, detected by the X-ray detectors 8L, 8R for position detection, are subjected to image processing and reconstructed into a three-dimensional image by the image processor 15. A filtered back projection method capable of high-speed processing is preferred as an algorithm for image reconstruction processing. In this way, the three-dimensional position coordinates and the shape of the treatment target are identified in real time (step 51). The set of irradiation conditions for the delivery of the initial therapeutic radiation are set on the basis of the data in the treatment plan (step 52). After the delivery of the initial therapeutic radiation (step 53), the delivered therapeutic radiation is detected by the first and second therapeutic radiation detectors 4, 5. The detection data is beam data on the therapeutic radiation before and after passing through the treatment target, and on the basis of this data, the dose absorbed by the treatment target and the dose distribution are calculated by the CPU 14. Furthermore, the first and second therapeutic radiation detectors 4, 5 detect the intensity, radiation field shape, and irradiation direction of the delivered therapeutic radiation. In the radiation therapy apparatus according to the present invention, the first and second therapeutic radiation detectors 4, 5 detect the delivered radiation at two points, thus making it possible to accurately calculate the irradiation direction of the therapeutic radiation and the radiation field shape on the treatment target. These types of data processing can achieve a processing speed of 1 ms to 2 ms through the use of a high-speed CPU or GPU and a high-speed memory. The data processed by the CPU 14 in real time is sequentially written in a storage device 13 (step 54).

Figure 7:
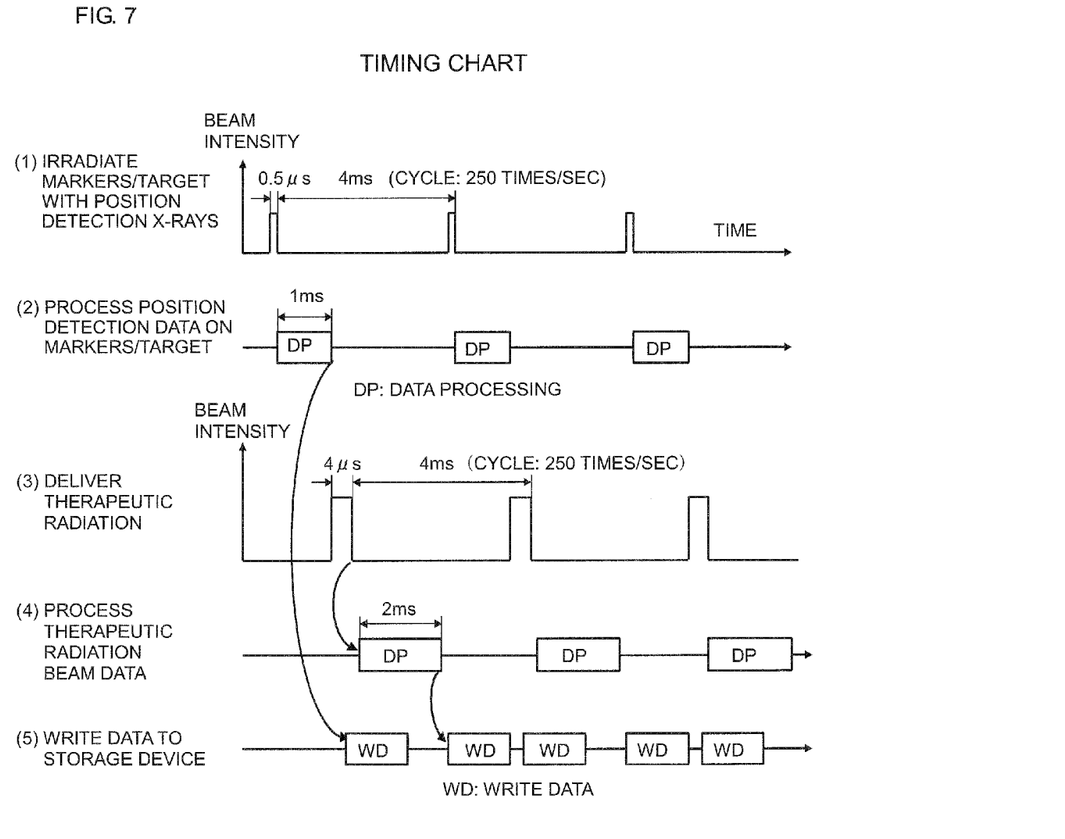
FIG. 7 is a timing chart showing operational timings of a radiation therapy apparatus according to the present invention.

Subsequently, for the delivery of the second therapeutic irradiation, low-energy X-ray irradiation is carried out toward the treatment target to image markers embedded in the vicinity of the treatment target and/or image the treatment target itself. The X-ray for position detection is delivered repeatedly at intervals of 4 ms, with a duration of 0.5 µs. The X-ray for imaging is detected by the X-ray detectors 8L, 8R for position detection. The imaging of the markers embedded in the vicinity of the treatment target and/or the treatment target itself and the processing of the detection data are executed in real time at intervals of about 4 ms, or about 250 times a second, which is more than adequate to track any movement of the treatment target due to breathing or the like of the patient. Therefore, the position and shape of the treatment target can be captured accurately for each delivery of therapeutic radiation. The detected image data and position data are subjected to image processing, and reconstructed into a three-dimensional image in real time by the image processor 15, and the data subjected to image processing is written in the storage device 13 (step 55). Next, on the basis of beam data such as the intensity, radiation field shape, irradiation direction, dose, and dose distribution of the initially delivered therapeutic radiation, data on the dose absorbed by the treatment target, and data on the position and shape the treatment target, the next set of irradiation conditions is set by the CPU 14 (step 56). Subsequently, the second therapeutic radiation is delivered (step 57). The standard delivery of therapeutic radiation is carried out about 250 times per second. The therapeutic radiation is delivered with a duration of 4 µs, and repeated at intervals of 4 ms. The delivered therapeutic radiation is detected by the first and second therapeutic radiation detectors 4, 5. The detection data is processed in real time by the CPU 14 and the image processor 15 as described above to output respective pieces of data: radiation field shape; irradiation direction; dose; and dose distribution, and data on the dose absorbed by the treatment target, etc. These pieces of data are sequentially written in the storage device 13 (step 58). Next, it is determined by the CPU 14 whether or not the radiation therapy is completed (step 59). If the radiation therapy has not been completed yet over the entire treatment target, the process returns to step 55 and steps 55 through 59 are repeated. If it is determined by the CPU 14 in step 59 that the radiation therapy has been completed over the entire treatment target, the radiation therapy is terminated automatically. In addition, if radiation is to be delivered to an area outside a predetermined therapeutic area due to a failure of the robot or due to a sudden movement of the treatment target in the course of radiation therapy, the delivery of radiation is stopped automatically by the CPU 14.

The radiation beam data acquired by a conventional radiation therapy apparatus has been only data on radiation prior to passing through a treatment target, as described above. Therefore, with respect to the radiation for each irradiation, it has not been possible to accurately assess the dose actually absorbed by the treatment target because there is no beam data on the X-ray prior to passing through the treatment target. By contrast, the radiation therapy apparatus according to the present invention includes the first and second therapeutic radiation detectors 4, 5, thus making it possible to acquire beam data on the radiation before and after passing through the treatment target for irradiation. With the aid of such data, the accurate irradiation direction, intensity, dose, absorbed dose, dose distribution, radiation field shape, etc., can be acquired for each irradiation. Moreover, the data is processed in real time immediately after detection and sequentially stored in the storage device 13, making the processing of the data dramatically easier than ever before. Accordingly, the burden of the verification after the therapy is substantially reduced.

As described above in detail, in the real-time three-dimensional radiation therapy apparatus according to the present invention, beam data on therapeutic radiation is acquired by the first and second therapeutic radiation detectors 4, 5 before and after the therapeutic radiation passes through the treatment target, and the delivery status of radiation and the therapy conditions can be thus known accurately. The iris collimator can adjust the diameter or breadth of the radiation field of the therapeutic radiation in a wide range of from 1 mm to 50 mm, and thus accurately deliver the radiation to the treatment target without causing damage to healthy tissue. Accordingly, a high dose of therapeutic radiation can be delivered at a time, and it is not necessary to carry out conventional separate irradiation. The data processing in the radiation therapy is executed in real time, and the radiation can be thus accurately delivered to the treatment target by tracking the movement of the treatment target. The tracking of the treatment target and the irradiation can be repeated in real time, thus eliminating the need for the development of a conventional detailed treatment plan, and further eliminating the need for the verification of the treatment plan prior to the treatment. The post-treatment verification can be easily carried out as needed using radiation beam data, etc. accumulated during treatment.

As described above, the real-time three-dimensional radiation therapy apparatus according to the present invention provides high-accuracy radiation therapy, and moreover can dramatically reduce the duration of therapy, thereby substantially reducing the burden on both the patient and the physician. As a result, it also becomes possible to reduce the cost of the radiation therapy.

Numerous additional modifications and variations are possible in light of the above teachings. It is therefore to be understood that, within the scope of the appended claims, the disclosure of this patent specification may be practiced otherwise than as specifically described herein.

What is claimed is:

1. A radiation therapy apparatus comprising:
   a first robot coupled to a robot head;
   a therapeutic radiation source attached to the robot head that radiates therapeutic radiation;
   a collimator for adjusting a radiation field shape of therapeutic radiation radiated from the therapeutic radiation source, attached to the robot head with the therapeutic radiation source disposed therebetween;
   a first therapeutic radiation detector attached to the robot head, with the therapeutic radiation source and the collimator disposed therebetween;
   a couch for supporting a patient;
   a second robot coupled to the couch for the patient, and configured to control a position and a posture of the support;
   a second therapeutic radiation detector that detects the radiation, disposed opposite the first therapeutic radiation detector, with the couch disposed between the first therapeutic radiation detector and the second radiation detector;
   at least two X-ray sources that emit low-energy X-rays for position detection toward at least one of a marker embedded in the vicinity of the treatment target and the treatment target itself, disposed proximal to the patient on the couch, installed either on the sides of the couch, or near the couch in a manner that can be controlled by the second robot;
   at least two X-ray detectors for position detection attached proximal to the patient and opposite the at least two X-ray sources, for detecting the X-rays emitted by the X-ray sources for position detection, each of the at least two X-ray detectors disposed opposite a corresponding one of the at least two X-ray sources with the couch interposed between the at least two X-ray sources and the at least two X-ray detectors;
   an image processor configured to reconstruct an image of the treatment target and to calculate position coordinates of the treatment target based on detection data from the at least two X-ray detectors;
   a central processing unit (CPU) for calculating beam intensity, irradiation direction, radiation field shape, dose, and dose distribution of the therapeutic radiation using detection data from the first therapeutic radiation detector and the second therapeutic radiation detector;
   a control unit for controlling the first robot, the second robot, the first and second therapeutic radiation detectors, the X-ray sources for position detection, and the X-ray detectors for position detection,
   wherein the first therapeutic radiation detector detects therapeutic radiation delivered from the therapeutic radiation source immediately after the therapeutic radiation passes through the collimator,
   wherein the second therapeutic radiation detector is proximal to the couch with the patient lying thereon and opposite the first therapeutic radiation detector with the couch interposed therebetween, the second therapeutic radiation detector configured to track movement of the therapeutic radiation source and detect therapeutic radiation after the therapeutic radiation has passed through the treatment target,
   wherein the CPU computes the intensity, irradiation direction, dose, and dose distribution of the therapeutic radiation, and dose absorbed by the treatment target, radiation field shape, and position of the treatment target in real time based on data output from the image processor and detection data from the X-ray detectors for position detection and from the first and second therapeutic radiation detectors, and feeds the calculation result back to a next irradiation of the therapeutic radiation in real time, and
   wherein the X-ray sources for position detection and the corresponding X-ray detectors for position detection are movable and controlled by the second robot so that irradiation directions and angles of the X-ray sources for position detection are symmetrically disposed on opposite sides of the treatment target of a patient on the couch.

2. The radiation therapy apparatus according to claim 1, wherein the robot for a therapeutic radiation source is one of a multi-axis arm-shaped robot, a gantry-shaped robot, a C-arm robot, and a robot with a C-arm attached to an arm end of the multi-axis arm-shaped robot, to support the therapeutic radiation source, the collimator, and the first therapeutic radiation detector.

3. The radiation therapy apparatus according to claim 2, wherein the second therapeutic radiation detector is supported by one of the gantry-shaped robot, the C-arm robot, and the robot with the C-arm attached to the arm end of the multi-axis arm-shaped robot.

4. The radiation therapy apparatus according to claim 1, wherein the collimator is one of an iris collimator and a multileaf collimator made of a heavy metal that continuously varies the shape of the beams emitted from the therapeutic radiation source.

5. The radiation therapy apparatus according to claim 1, wherein the collimator adjusts the diameter or breadth of the beams emitted from the therapeutic radiation source to provide a radiation field of from 1 mm to 50 mm in diameter or breadth on the treatment target.

6. The radiation therapy apparatus according to claim 1, wherein the collimator adjusts the diameter or breadth of the beams emitted from the therapeutic radiation source to provide a radiation field of from 1 mm to 10 mm in diameter or breadth on the treatment target.

7. The radiation therapy apparatus according to claim 1, wherein the therapeutic radiation is delivered at rate of about 250 times/second.

8. A radiation therapy method, comprising the steps of:
   executing, in real time, a step of identifying a position and a shape of a marker and/or a treatment target using X-ray sources for position detection and X-ray detectors for position detection;
   setting a set of irradiation conditions for therapeutic radiation;
   delivering the therapeutic radiation toward the treatment target from a therapeutic radiation source;
   acquiring beam data on the therapeutic radiation by first and second therapeutic radiation detectors;
   updating a next set of irradiation conditions in real time on the basis of the beam data on the therapeutic radiation acquired in the acquiring step; and
   storing, in a storage device, data output from the X-ray detectors for position detection and the first and second therapeutic radiation detectors.

9. The radiation therapy method according to claim 8, wherein the set of irradiation conditions is updated on the basis of detection data from the X-ray detectors for position detection and detection data from the first and second therapeutic radiation detectors,
   the method further comprising the step of stopping the delivery of therapeutic radiation from the therapeutic radiation source if the next irradiation area falls outside the treatment target.

10. The radiation therapy method according to claim 8, further comprising the step of using the detection data from the X-ray detectors for position detection and the first and second therapeutic radiation detectors stored in the storage device to verify the results of radiation therapy.

11. The radiation therapy method according to claim 8, wherein the step of delivering the therapeutic radiation is repeated about 250 times/second.

* * * * *